United States Patent [19]

Haase et al.

[11] 3,987,074
[45] Oct. 19, 1976

[54] PROCESS FOR THE MANUFACTURE OF VANADYL ALCOHOLATES

[75] Inventors: Ranier Haase, Bokel(Oldenburg); Arnold Lenz, Cologne-Stammheim, both of Germany

[73] Assignee: Dynamit Nobel Aktiengesellschaft, Troisdorf, Germany

[22] Filed: Aug. 21, 1974

[21] Appl. No.: 499,251

[30] Foreign Application Priority Data
Aug. 25, 1973 Germany............................ 2343056
Dec. 17, 1973 Germany............................ 2362704

[52] U.S. Cl. ........................ 260/429 R; 252/431 R
[51] Int. Cl.² ............................................ C07F 9/00
[58] Field of Search ................................. 260/429 R

[56] References Cited
UNITED STATES PATENTS

| | | | |
|---|---|---|---|
| 3,432,445 | 3/1969 | Asgan ........................ | 260/429 R X |
| 3,455,974 | 7/1969 | Liong Su ...................... | 260/429 R |
| 3,652,617 | 3/1972 | Termin et al. ................ | 260/429 R |
| 3,657,295 | 4/1972 | McCoy ........................... | 260/429 R |

FOREIGN PATENTS OR APPLICATIONS

| | | |
|---|---|---|
| 1,271,641 | 1/1962 | France |
| 1,816,386 | 2/1970 | Germany |

OTHER PUBLICATIONS

Bull. Acad. Sci. USSR pp. 899–900 (1957).

*Primary Examiner*—Helen M. S. Sneed
*Attorney, Agent, or Firm*—Burgess, Dinklage & Sprung

[57] ABSTRACT

A process for the preparation of a vanadyl alcoholate which comprises contacting vanadium pentoxide with an alcohol in the presence of an orthoester of the formula $R' \cdot C(OR'')_3$ wherein:

R' is hydrogen, a straight-chained alkyl group of 1 to 5 carbon atoms or a branched chain alkyl group of 1 to 5 carbon atoms; and
R'' is a straight-chained alkyl group of 1 to 12 carbon atoms, a branched-chain alkyl group of 1 to 12 carbon atoms or phenyl.

12 Claims, No Drawings

PROCESS FOR THE MANUFACTURE OF VANADYL ALCOHOLATES

BACKGROUND OF THE INVENTION

1. Field of the Invention

This invention relates to a process for the preparation of vanadyl alcoholates, particularly vanadyl alcoholates of the formula: $O=V(OR)_3(Y)_n$ wherein Y is $\equiv V=O$ and $n$ is 0 or 1 and when $n$ is O, R is alkyl, cycloalkyl, alkylaryl, arylalkyl, aryl, alkoxyaryl or hydroxyalkyl and when $n$ is 1, R is an alkoxy radical. This invention is particularly addressed to the problem of removing water formed during the preparation of vanadyl alcoholates by reaction of vanadyl pentoxide with an alcohol. This invention is also directed to the preparation of vanadyl alcoholates of high purity.

2. Description of the Prior Art

It is known that vanadium pentoxide can be reacted with alcohols to form the corresponding vanadyl alcoholates according to the following reaction:

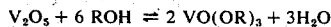
$$V_2O_5 + 6\ ROH \rightleftharpoons 2\ VO(OR)_3 + 3H_2O$$

Since this reaction is an equilibrium reaction it is necessary, in order to favor the formation of esters, to continually remove the water that forms. The continual removal of the water, however, involves great difficulty.

It is known to remove the water by distilling over the water as it forms in the reaction, together with excess alcohol, into a second reaction vessel containing a substance which absorbs water, such as quicklime for example. At the boiling temperature of the alcohol, and with intensive stirring, the alcohol is dewatered in the second reaction vessel and then distilled back into the first reaction vessel in which the reaction with vanadium pentoxide is taking place. (Cf. German Offenlegungsschrift 1,816,386).

This known process, however, is very expensive. For example, the water-removing substance must be constantly replaced or regenerated. Also, constant vigilance is necessary during the reaction to prevent the reaction from stopping prematurely due to the exhaustion of the water-removing substance. Heat must continually be introduced into the mixture captured in the second reaction vessel in order to keep it boiling. This relatively great energy consumption is particularly appreciable when operating on a commercial scale.

Another disadvantage of this known process consists in the fact that it is necessary to operate in the presence of a strongly acid catalyst. Despite the presence of the catalysts, however, it is necessary to reflux the reaction mixture for more than 8 hours as a rule if it is desired to achieve pure ester yields of about 50%. Yields greater that 50% can be achieved only when operating on a laboratory scale. When the procedure is used on a commercial scale it is found that the yields vary from batch to batch. Consequently, the prior-art process does not achieve reproducible results to a sufficient extent.

Operating in the presence of strongly acid catalysts results in additional disadvantages. The amounts of acid added accelerate the reaction of the $V_2O_5$ with the alcohol to form the ester, and yet they promote the reduction of the pentavalent vanadium to tetravalent vanadium with the cooperation of the corresponding alcohol. The side reaction, however, is not desired.

Since the compounds of the strongly acid reaction are used in practice preferably in amounts of 1 to 10 weight percent with reference to the input vanadium, they are not present in only catalytically effective amounts. Rather, they are present in appreciable percentages which constitutes an impurity in the reaction mixture product. Thus, sulfuric acid is usually found in the form of vanadyl sulfate, in which the vanadium is in the oxidative tetravalent stage. Thus, for example, in a solution of vanadium oxytriisopropylate in isopropanol, with a moisture content of 0.2 weight percent the main part of the tetravalent vanadium is found in the form of solid vanadyl sulfate in the unreacted vanadium pentoxide. In the case of higher moisture contents, the vanadyl sulfate is contained increasingly in the reaction mixture and interferes with the processing.

For example, out of 200 g of $V_2O_5$, 3000 ml. of isopropanol and 10 ml. of concentrated sulfuric acid, one obtains after 3 hours of reaction solution which still contains 0.39 weight percent of water. When the unreacted $V_2O_5$ is filtered out of the solution and the isopropanol has been removed by evaporation and the ester has been vacuum distilled, 143 g (= 26% yield) of pure vanadium oxytriisopropylate is obtained. An extraordinarily great quantity of 109 g of distillation residue remains as an unwanted by-product probably due to the high percentage of sulfuric acid and the excessively great moisture content of the reaction solution.

If organic sulfonic acids, such as toluenesulfonic and benzenesulfonic acid, are used instead of sulfuric acid, similar phenomena occur. In the preparation of vanadium oxytriisopropylate, voluminous greenish flakes precipitate from the greenish reaction solution during the progressive concentration and the distillative refinement of the ester that follows; these flakes interfere with the distillation and increase the percentage of distillation residue.

Attempts have already been made to use phenol derivatives or weak acids such as boric acid, for example, as catalysts instead of the strong acids. In the reaction of alcohols having up to 4 carbon atoms, however, these catalysts display no activity (French Pat. 1,271,641).

It is also known in the preparation of vanadyl alcoholates to reflux stoichiometric amounts of vanadium pentoxide and an alcohol having 5 to 5 carbons, respectively, in the presence of benzene (with a ratio of alcohol to benzene of 1 : 1.1 to 1 : 1.35 by volume). The water formed at the boiling temperature is removed from the reaction zone as an azeotropic mixture by the addition of benzene and can then be separated as the heavy phase in a water separator.

At a reaction time of 8 to 12 hours the yields amount to only between 10 and 32% with reference to the vanadium pentoxide input. Especially in the preparation of vanadium oxitri-n-butylate, yields of only 26%, for example, have been achieved (cf. Bull. Acad. Sci. USSR 1957, pages 899–900).

In the preparation of vanadium oxitri-n-butylate it has also been proposed to add toluene instead of benzene to the reaction mixture as an extractant in order to increase the yield. Yields of up to about 65% can be achieved by this process (cf. U.S. Pat. No. 3,657,295), but the time required for the reaction is very long, amounting to as much as 24 hours. In this process a mixture of vanadium pentoxide, toluene and n-butanol is heated to ebullition and the water forming in the reaction is distilled together with the toluene as an azeotropic mixture into a water separator. Here a water-rich phase and a hydrocarbon-rich phase are formed. The latter is continuously recycled to the reactor and the water-rich phase is separated at intervals. Using 1.3 to 1.4 times the stoichiometrically required amount of alcohol, the highest yields are achieved in this case, of 65%. According to this patent, the use of a greater excess of alcohol will not achieve any technical effect as regards increasing the yield, increasing the reaction speed, or the like.

The long reaction time (24 hr.) that is required if it is desired to achieve yields of 65% is particularly disadvantageous. Another disadvantage is that very large amounts of toluene must be used (the ratio of toluene to n-butanol is preferably to be from 1 : 1 to 3 : 1 by volume). In the processing of the reaction mixture that follows, the excess solvent — in this case unreacted alcohol together with toluene — is removed by distillation. It has been found disadvantageous that, before the distillate can be used for the next batch, it must first be readjusted to a specific toluene-butanol content, because otherwise reproducible results cannot be achieved. For this purpose, however, complicated procedures are necessary, which make this process uneconomical and render technical scale operation difficult.

To avoid these difficulties in the prior art methods based on the reaction of $V_2O_5$ with alcohols it has also been proposed that vanadyl alcoholates be prepared by starting out with $VOCl_3$ and reacting it with alkali metal alcoholates or alcohols; this results in yields of 60% (with reference to $VOCl_3$). These known methods, however, have the disadvantage that the reactant $VOCl_3$, which is very sensitive to hydrolysis, has to be prepared in a separate procedure from $V_2O_5$. Furthermore, undesired vanadium-containing by-products form in this process, as well as alkali chlorides or HCl as reaction products. The hydrochloric acid that forms has to be neutralized with ammonia in an another separate procedure, so that, by and large, the process is a very complicated one. In addition, these prior-art methods result in products which are not entirely chloride-free. The esters prepared in this manner usually have a reduced shelf life, which is indicated by a dark discoloration. Often they are then no longer suitable for use as a component of a polymerization catalyst.

The preparation of vanadyl alcoholates of $C_2$ to $C_4$ alcohols by the transesterification of a lower vanadyl alcoholate with a correspondingly higher boiling alcohol is relatively difficult. These transesterification methods require that the starting product be a vanadyl alcoholate of a low alcohol which in turn is supposed to be more easily accessible than the desired vanadyl alcoholate of a higher alcohol. For the preparation of such "low" alcoholates, however, a process like the one described above (on the basis of $VOCl_3$) has hitherto been recommended. In the transesterification processes, losses of yield have always had to be accepted in order to prepare pure esters, so that the problem of manufacturing pure esters with a high space-time yield, by the use of a very simple method, has basically not yet been solved.

It is, therefore, an object of the present invention to provide a process for the preparation of vanadyl alcoholates starting with vanadyl pentoxide. It is a particular object of the present invention to prepare vanadyl alcoholates in high purity in good yields within a commercially feasible period of time and especially without the use of separate reaction zones, recycling procedures and the like. It is a particular object of the present invention to provide a process by which those vanadyl alcoholates which have heretofore proved difficult to prepare can be synthesized in high purity and within commercially feasible period of time with respect to space-time yield.

SUMMARY OF THE INVENTION

The objects of the present invention are provided by a process for the preparation of a vanadyl alcoholate which process comprises contacting vanadium pentoxide with an alcohol in the presence of an orthoester of the formula $R' . C(OR'')_3$ wherein R' is hydrogen, a straight-chained alkyl group of 1 to 5 carbon atoms or a branched chain alkyl group of 1 to 5 carbon atoms; and R'' is a straight-chained alkyl group of 1 to 12 carbon atoms, a branched-chain alkyl group of 1 to 12 carbon atoms or phenyl.

The present invention can be considered to be an improvement over the art known process for the preparation of vanadyl alcoholates wherein vanadium pentoxide is reacted with an alcohol. The improvement comprises including in the reaction mixture an orthoester of the formula $R' . C(OR'')_3$ wherein R' and R'' have the previous assigned significance.

It has been found, in accordance with the present invention, that if an orthoester of such formula is included in a reaction mixture containing vanadium pentoxide and an alcohol that the water formed during the reaction is taken up by the orthoester which, in turn, is hydrolyzed to form an ester an an alcohol.

The invention can be more readily understood when reference is made to the general equation for the reaction of vanadium pentoxide and an alcohol which equation is as follows:

$$V_2O_5 + 6 ROH \rightleftharpoons 2 VO(OR)_3 + 3 H_2O \qquad 1.$$

The alcohol is generally employed during this reaction in at least a stoichiometric amount and preferably it is present in excess. The water produced by the reaction would normally present problems in carrying out the process for the water must be removed if the reaction is to proceed to high yields. By including an orthoester of the type described in the reaction mixture, the water is immediately taken up by the orthoester, which, in turn, is hydrolyzed to formic acid esters or to the carboxylic acid ester and the corresponding alcohol, as the case may be, in accordance with the following equation:

$$R' . C(OR'')_3 + H_2O \rightarrow R'COOR'' + 2 R''OH. \qquad 2$$

DESCRIPTION OF SPECIFIC EMBODIMENTS

In a preferred embodiment of the process of the invention, an orthoester is used which upon hydrolysis releases the same alcohol whose vanadyl alcoholate is to be prepared.

Examples of orthoesters are: orthoformic acid esters such as, for example, trimethyl or triethyl orthoformiate triisoamyl orthoformiate, tripropyl orthoformiate, triphenyl orthoformiate and the like, as well as the corresponding orthoesters of acetic acid, propionic acid, butyric acid and the like. In general, these orthoesters are used which are soluble in the particular reaction mixture that is prepared.

The formic acid ester, or the carboxylic acid ester such as acetic acid methyl ester or propionic acid methyl ester or acetic acid ethyl ester as the case may be, may remain in the reaction mixture until the end of the reaction of the $V_2O_5$, together with the excess alcohol if any, and the inert organic solvent if any has been added; the low-boiling components, however, are usually distilled away in the course of the reaction, preferably through a column, to prevent the temperature of the reaction mixture from dropping below a certain value which is the optimum for the particular reaction.

In the reaction of vanadium pentoxide with alcohol, it is also possible in accordance with the invention to use an orthoester which upon hydrolysis does not release the same alcohol as the one whose vanadyl alcoholate is to be prepared. If the radicals R in the vanadyl alcoholate are to be identical, it is desirable to remove continually from the reaction mixture the low alcohol that is released. It is advantageous in this case to perform the reaction at the boiling temperature of the reaction mixture in a reaction vessel that is preferably equipped with a column. At the top of the column the low alcohol can be removed, in the form of an azeotrope with the formic acid ester or carboxylic acid formed, if desired, and with the inert solvent if any has been added.

In the process of the invention trimethyl orthoformate or triethyl orthoformate is preferred as the orthoester. These orthoesters are easily accessible on the one hand, and on the other hand they are especially well suited for the purpose of rendering harmless the water formed in the reaction of the vanadium pentoxide with the alcohol. When used in the manner described, they are vitually inert in relation to the vanadyl alcoholates that are formed, as are the corresponding formic acid esters which, as described, can be removed from the reaction mixture during or after the reaction. However, it is to be considered that, parallel with the reaction of the trimethyl orthoformate or triethyl orthoformate with the water, a transesterification reaction with the higher (= higher-boiling) alcohol is constantly taking place, although it has no harmful effect on the vanadyl alcoholate that is to be produced.

The alcohol reacting with the vanadium pentoxide in accordance with reaction equation 1 can be, for example, a $C_1$ to $C_{12}$ alkanol, which can be branched if desired, such as methanol, ethanol, isopropanol, amyl alcohol and its isomers, etc. Longer-chained alkanols, such as lauryl alcohol for example, may also be used. Also, cyclohexanol or phenols as well as bifunctional alcohols such as ethylene glycol, may be used. Generally the alcohol has 1-12 carbon atoms.

The following vanadyl alcoholates, for example, may be prepared directly by the method of the invention: vanadyl trimethylate, vanadyl triethylate, vanadyl triisopropylate, vanadyl tri-n-propylate, vanadyl tri-n-butylate, vanadyl trisecondarybutylate, vanadyl tritertiarybutylate, vanadyl triisoamylate, and the vanadyl trialcoholates of the other isomers of amyl alcohol, vanadyl trilaurate, vanadyl tricyclohexanolate, vanadyl trimethylglycolate, vanadyl triphenolate, vanadyl glycolate $(O = V(OCH_2-CH_2O)_3-V=O)$ etc.

The term "vanadyl alcoholate" in the meaning of the invention is to include the corresponding phenolates, and the term "alcohol" is to include the corresponding phenols.

The method of the invention is especially suitable for the manufacture of vanadyl alcoholates on the basis of methanol and ethanol, which have hitherto been able to be prepared directly and in high purity only with difficulty.

In accordance with Equation 1, the alcohol may be used in stoichiometric amounts with respect to the input $V_2O_5$. Preferably, however, it is added in excess, especially when an orthoester on the basis of a low-boiling alcohol is used in the reaction of $V_2O_5$ with a higher boiling alcohol. It is desirable to use the water-free reaction components. However, small percentages of water are generally not objectionable since they are intercepted by the orthoester.

In the process of the invention, the orthoester can be added progressively, i.e., accordingly as the reaction progresses, but usually the full amount is added at the beginning of the reaction, and preferably in an excess, but at least in a molar ratio of 1 : 2 to 1 : 0.5 with respect to the water that is released in theory in the reaction of vanadium pentoxide with the alcohol that is used.

The vanadium pentoxide used in the method of the invention is preferably in fine powder form. The reaction is performed at elevated temperature, and if desired inert organic compounds are added, such as benzene, toluene or carbon tetrachloride, which serve on the one hand as solvents and on the other hand they serve the purpose of adjusting the boiling point of the reaction mixture to a certain temperature level. Generally speaking, the process is carried out at a temperature C. from the boiling point of the reaction mixture.

The reaction can be carried out at subatmospheric pressure. It can also be carried out at super atmospheric pressures. However, it is preferably carried out at normal atmospheric pressure.

When low-boiling alcohols are used, such as for example the aliphatic $C_1$ to $C_6$ alcohols, the reaction is preferably performed at the boiling temperature of the reaction mixture, while the reaction vessel is best equipped with a separating column of, for example, 10 practical trays. The low-boiling mixtures can be taken off at the superimposed column head consisting, among other things, of a reflux condenser and a temperature measuring device.

The reactants are reacted preferably with intensive stirring for several hours, e.g., 8 to 16 hours. When the reaction has ended, the reaction mixture, still hot if desired, can be separated from the unreacted vanadium pentoxide by decanting or filtering.

If the vanadyl alcoholate that has formed is insoluble or poorly soluble in the reaction mixture, a solvent such as carbon tetrachloride, or a hydrocarbon such as benzene, toluene or the like, which will increase the solubility of the alcoholate can be added to the reaction mixture before the reaction begins in some cases or after it has ended in others. After the unreacted vanadium pentoxide has been filtered out, the solution is concentrated, at reduced pressure if desired. In many cases, in which the vanadyl alcoholate is a solid substance, e.g., vanadyl trimethylate, it is concentrated by evaporation to the dry state and the vanadyl alcoholate can be isolated as the residue. If necessary, the vanadyl alcoholate may be refined by recrystallization or sublimation in vacuo.

In cases in which a vanadyl alcoholate that is fluid is prepared, it is desirable to subject the filtrate to a fractional distillation at reduced pressure, in which case overheating of the wall of the flask is to be avoided and provision must be made for thorough mixing of the contents of the flask, since the vanadyl alcoholates are thermally unstable. For the isolation of the pure vanadyl alcoholates the distillation is usually performed with the use of a small column. The distillation residue in the distillative refinement is in most cases extremely small under these circumstances.

The unreacted vanadium pentoxide remaining in the reaction with low-boiling alcohols such as ethanol contains tetravalent vanadium on only a negligible scale. Since the formation of tetravalent vanadium is largely proportional to the temperature of the reaction mixture, the addition of an inert organic solvent serves to reduce the temperature in the reaction mixture, especially in the preparation of vanadyl alcoholates of higher-boiling alcohols.

The vanadyl alcoholates prepared by the method of the invention are very pure having a purity of at least 95% by weight, especially 99%. They are anion-free and stable in storage.

On account of their high degree of purity they are especially well suited for use as catalysts, e.g., as a component of Ziegler catalysts for the polymerization especially of ethylene with propylene. They may also be used in many other reactions, as for example in condensation polymerizations.

The unreacted vanadium pentoxide is relatively pure in the process of the invention and it is not necessary to regenerate it after each batch. Instead, it may be used repeatedly for additional reactions.

Afterward it is advantageous to regenerate the vanadium pentoxide that remains after several reactions. By thermal treatment at preferably about 300° to 400° C. under the influence of air or oxygen, the unreacted vanadium pentoxide which has meantime become somewhat sluggish can be restored to full reactivity for the reaction of the invention.

In order to more fully illustrate the nature of the invention and the manner of practicing the same, the following Examples are presented:

EXAMPLE 1

In a three-necked flask (capacity 6 liters) provided with a reflux condenser, 200 g (2.75 moles) of $V_2O_5$, 2500 ml. (62 moles) of methanol and 655 g (6.2 moles) of trimethyl orthoformate were placed. The mixture was heated for 8 hours at ebullition with constant stirring. Upon cooling, yellow crystals of vanadyl trimethylate formed on the walls of the flask. To separate the vanadyl trimethylate from the unreacted vanadium pentoxide, the flask contents were filtered in the hot state in which most of the vanadyl trimethylate is in solution. The filtrate was freed of excess methanol and trimethyl orthoformiate at reduced pressure and elevated temperature. 218 g of vanadyl trimethylate was obtained in the form of yellow crystals.

Yield: 25% with reference to the vanadium pentoxide charged.

EXAMPLE 2

500 g of vanadium pentoxide (2.75 moles), 2100 ml. of ethanol (36 moles) and 734 g of triethyl orthoformiate (5 moles) were placed in a three-necked flask of a capacity of 6 liters. The mixture was heated at ebullition with stirring. The three-necked flask was equipped with a separating column (10 practical trays) and a superimposed column head.

At the column head a mixture boiling at 53° C. was removed, which was an azeotrope consisting of formic acid ethyl ester and ethyl alcohol. Later, as more of the easier boiling component was removed, the temperature at the head of the column rose to 77° C.

After 16 hours of heating the contents of the flask was processed. The unreacted vanadium pentoxide was filtered out and the filtrate was first freed of excess ethanol at reduced pressure and elevated temperature. By means of a separating column (5 practical trays) the separation of the triethyl orthoformiate from the pure vanadyl triethylate (95° C/12 Torr) was performed at 42° C./12 Torr.

The yield was 38% with reference to the vanadium pentoxide charged.

The ratio of pure ester to distillation residue was 43 : 1 (in parts by weight). This calculates to a purity of about 98%.

EXAMPLE 3

The procedure was similar to Example 2, but the reaction was performed with the addition of trimethyl orthoformiate instead of triethyl orthoformiate. Thus 500 g of vanadium pentoxide (2.75 moles) was heated at ebulliation with 3100 ml. of ethanol (53 moles) and 655 g of trimethyl orthoformiate (6.2 moles). The light-boiling substance was again removed at the head of the column starting at about 50° C. and up to about 76° C. After 16 hours of reaction time the mixture was processed as in Example 2.

Yield: 48%

The ratio of pure ester to distillation residue was 53 : 1 (parts by weight). This calculates to a purity of about 98%.

EXAMPLE 4

In an apparatus like the one in Example 2, 500 g. $V_2O_5$ (2.75 moles) was heated at ebullition with 3100 ml. isopropanol (41 moles) and 873 g trimethyl orthoformiate (8.25 moles). At the top of the column an azeotropic mixture of formic acid isopropyl ester and methanol was removed at 57° C., and later only methanol was taken out. After 16 hours of reaction the processing and distillative refinement were performed as described in the previous examples.

Yield of vanadyl triisopropylate: 48%.

The ratio of pure ester to distillation residue was 100 : 1 (parts by weight). This calculates to a purity of 99%.

EXAMPLE 5

As in Example 2, 500 g of vanadium pentoxide (2.75 moles), 2500 ml. of n-butanol (27 moles) and 916 g of triethylorthoformiate (6.2 moles) were heated at ebullition. An azeotropic mixture of formic acid ethyl ester and ethanol was taken out at the head of the column at 55° C. to 78° C., but later only ethanol was taken out; still later the temperature at the head of the column rose to 107° C. After 8 hours the mixture was processed and pure vanadyl tri-n-butylate was obtained in a yield of 53%.

The ratio of pure ester to distillation residue was 82 : 1 (parts by weight). This calculates to a purity of about 98.8%.

EXAMPLE 6

In a three-necked flask of 6 liters capacity 500 g of vanadium pentoxide (2.75 moles), 3100 ml. of ethanol (53 moles) and 740 g of acetic acid orthomethyl ester (6.8 moles were placed. The mixture was heated at ebullition with stirring. The three-necked flask was equipped with a separating column (10 practical trays) and a superimposed column head.

At the beginning, a mixture boiling at 57° C. was taken out, consisting of acetic acid methyl ester and methanol. Later, as removal of the easier boiling components continued, the temperature at the head of the column rose to 74° C. After 16 hours of heating the contents of the flask were processed. The unreacted vanadium pentoxide was filtered out and the filtrate was first freed of the excess ethanol at reduced pressure and elevated temperature. The separation of the excess acetic acid orthoethyl ester formed during the reaction was performed by means of a separating column (5 practical trays) at 42° C/12 Torr from the pure vanadyl triethylate (95° C/12 Torr).

The yield amounted to 40.5% with reference to the vanadium pentoxide.

The ratio of pure ester to distillation residue was 21 : 1.

EXAMPLE 7

In an apparatus like that of Example 1, 500 g of vanadium pentoxide (2.75 moles) was heated at ebullition with 3100 ml. of isopropanol (41 moles) and 740 g of acetic acid orthomethyl ester (6.8 moles). At the beginning an easier boiling fraction was taken out at the head of the column at 57° C; later, as removal continued, the boiling point at the head increased to 80° C. In all, 1.2 liters of distillate were removed. After 16 hours of reaction the processing and refinement by distillation were performed as in the preceding example. Yield: 40.5% of pure vanadyl triisopropylate. The ratio of pure ester to distillation residue was 54 : 1.

EXAMPLE 8

As in Example 1, 500 g of vanadium pentoxide (2.75 moles), 3100 ml. of n-butanol (33.5 moles) and 740 g of acetic acid orthomethyl ester (6.8 moles) were heated at ebullition. At the beginning an easier-boiling fraction was removed at the column head at approximately 57° C. As removal continued the temperature at the head rose over a period of 8 hours to 115° C. Then the mixture was processed as in the above examples. Very pure vanadyl n-butylate was obtained in a yield of 57%. The ratio of pure ester to distillation residue was 27 : 1.

EXAMPLE 9

In an apparatus similar to that of Example 1, 500 g of vanadium pentoxide (2.75 moles) was heated at ebullition with 3100 ml. of ethanol (53 moles) and 1000 g of acetic acid orthoethyl ester (6.7 moles). Soon an easier-boiling fraction could be taken out at the top at 72° C. and consisted substantially of acetic acid ethyl ester. After 16 hours of reaction time, 1 liter of distillate had been taken out and the temperature at the column head had risen to 76° C. Then the mixture was processed as in Example 1. Pure vanadyl ethylate was obtained in a yield of 33%. The ratio of pure ester to distillation residue was 28 : 1.

What is claimed is:

1. A process for the preparation of a vanadyl alcoholate which comprises contacting vanadium pentoxide with a cyclic or acyclic mono or bifunctional alcohol of 1 to 12 carbon atoms in the presence of an orthoester of the formula $$R' \cdot C(OR'')_3$$

wherein
  R' is hydrogen, a straight-chained alkyl group of 1 to 5 carbon atoms or a branched-chain alkyl group of 1 to 5 carbon atoms; and R'' is a straight-chained alkyl group of 1 to 12 carbon atoms, a branched-chain alkyl group of 1 to 12 carbon atoms or phenyl.

2. A process according to claim 1 wherein the process is carried out in the presence of an inert solvent.

3. A process according to claim 1 wherein the process is carried out at the boiling point of the reaction mixture.

4. A process according to claim 1 wherein said orthoester is trimethyl orthoformiate, triethyl orthoformiate, triphenyl orthoformiate, triamyl orthoformiate, triisoamyl orthoformiate, tri-tert.-amyl orthoformiate, tripropyl orthoformiate, trimethyl orthoacetate, triethyl orthoacetate, triphenyl orthoacetate, triamyl orthoacetate, tri-tert.-amyl orthoacetate, triisoamyl orthoacetate, tripropyl orthoacetate, trimethyl orthopropionate, triethyl orthoproprionate, triphenyl orthopropionate, triisoamyl orthoproprionate, tripropyl orthoproprionate, trimethyl orthobutyrate, triethyl orthobutyrate, triphenyl orthobutyrate or tripropyl orthopropionate.

5. A process according to claim 1 wherein said alcohol is a $C_1 - C_{12}$ alkanol.

6. A process according to claim 1 wherein said alcohol is methanol, ethanol, propanol, isopropanol, n-butanol, sec.-butanol, tert.-butanol, amyl alcohol, an isomer of amyl alcohol, cyclohexanol, lauryl alcohol, phenol or ethylene glycol.

7. A process according to claim 1 wherein the orthoester is introduced progressively to the reaction mixture as water is produced by reaction of said vanadyl pentoxide with said alcohol.

8. A process according to claim 1 wherein the process is carried out for from 8 to 16 hours.

9. A process according to claim 2 wherein said solvent is carbon tetrachloride or a hydrocarbon.

10. A process according to claim 9 wherein said solvent is a hydrocarbon and said hydrocarbon is benzene or toluene.

11. A process according to claim 1 wherein said orthoester is present in a molar amount such that the molar ratio of orthoester to water theoretically produced by reaction of the vanadyl pentoxide with alcohol is from 1 : 2 to 1 : 0,5.

12. A vanadyl alcoholate of the formula $O=V(OCH_2-CH_2O_3-V=O$.

* * * * *

UNITED STATES PATENT AND TRADEMARK OFFICE
CERTIFICATE OF CORRECTION

PATENT NO. : 3,987,074
DATED : OCTOBER 19, 1976
INVENTOR(S) : RAINER HAASE and ARNOLD LENZ It is certified that error appears in the above-identified patent and that said Letters Patent are hereby corrected as shown below:

[75] "Ranier" should read -- Rainer --; "Bokel (Oldenburg)" should read -- Bokel/Oldenburg --.

Claim 12, the formula should read -- $O=V(OCH_2-CH_2O)_3-V=O$ --.

Signed and Sealed this

Fifth Day of April 1977

[SEAL]

Attest:

RUTH C. MASON
*Attesting Officer*

C. MARSHALL DANN
*Commissioner of Patents and Trademarks*